United States Patent
Tsunoda et al.

(10) Patent No.: US 11,167,120 B2
(45) Date of Patent: Nov. 9, 2021

(54) MEDICAL DEVICE AND MANUFACTURING METHOD THEREOF

(71) Applicant: TERUMO KABUSHIKI KAISHA, Tokyo (JP)

(72) Inventors: Ken Tsunoda, Minami-Alps (JP); Toshihiko Kakinoki, Showa-cho (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 42 days.

(21) Appl. No.: 16/231,364

(22) Filed: Dec. 21, 2018

(65) Prior Publication Data

US 2019/0240473 A1 Aug. 8, 2019

(30) Foreign Application Priority Data

Dec. 28, 2017 (JP) .............................. JP2017-254435

(51) Int. Cl.
*A61M 39/06* (2006.01)
*A61M 39/26* (2006.01)
*A61M 39/02* (2006.01)
*A61M 39/10* (2006.01)
*A61M 39/00* (2006.01)

(52) U.S. Cl.
CPC ............ *A61M 39/06* (2013.01); *A61M 39/26* (2013.01); *A61M 2039/0036* (2013.01); *A61M 2039/0202* (2013.01); *A61M 2039/0205* (2013.01); *A61M 2039/064* (2013.01); *A61M 2039/1072* (2013.01)

(58) Field of Classification Search
CPC .. A61M 2039/0063; A61M 2039/0072; A61M 2039/1072
See application file for complete search history.

(56) References Cited

U.S. PATENT DOCUMENTS

| | | | |
|---|---|---|---|
| 2007/0112311 A1* | 5/2007 | Harding | A61M 39/045 604/246 |
| 2007/0112314 A1 | 5/2007 | Harding | |
| 2014/0332091 A1* | 11/2014 | Ueda | A61M 39/26 137/15.18 |
| 2016/0015958 A1* | 1/2016 | Ueda | A61M 39/10 604/537 |

FOREIGN PATENT DOCUMENTS

| | | |
|---|---|---|
| JP | S58-188456 A | 11/1983 |
| JP | 2015-221108 A | 12/2015 |
| WO | WO-2010/122988 A1 | 10/2010 |

OTHER PUBLICATIONS

Office Action dated Aug. 3, 2021 issued in counterpart Japanese Patent Application No. 2017-254435, (10 pages).

* cited by examiner

*Primary Examiner* — Emily L Schmidt
(74) *Attorney, Agent, or Firm* — Foley & Lardner LLP

(57) ABSTRACT

A medical device includes: a first member including: a body portion, and an anchor, wherein a resin material of the anchor is different from a resin material of the body portion, and wherein the anchor is interlinked to the body portion; and a second member including a connecting portion that is connected to the anchor, wherein a resin material of the second member is the same as the resin material of the anchor.

7 Claims, 12 Drawing Sheets

MEDICAL DEVICE AND MANUFACTURING METHOD THEREOF

CROSS-REFERENCE TO RELATED APPLICATION

The present application claims priority to Japanese Appl. No. 2017-254435, filed on Dec. 28, 2017, the contents of which are hereby incorporated by reference in their entirety.

BACKGROUND

The present disclosure relates to a medical device and a manufacturing method thereof.

A known example of a medical device used for the purpose of infusion or blood sampling is a medical device that includes an internal channel. For example, JP 2015-221108 A discloses a medical device provided with a single-piece channel member that faces a channel, a single-piece non-channel member that does not face the channel, and a valve body sandwiched and held by the channel member and the non-channel member. The non-channel member and the channel member are welded together.

SUMMARY

In a medical connector of the related art, such as that disclosed in JP 2015-221108 A, typically, a non-channel member includes a resin material that is the same as that of a channel member, from a viewpoint of ensuring connection strength between the non-channel member and the channel member. However, the channel member is required to include a resin material compatible with a fluid flowing through the channel. That limits the choice of materials for the non-channel member. For example, when the channel member includes polypropylene (PP), which has excellent chemical resistance, the non-channel member also includes PP. However, making the non-channel member with PP may cause difficulty in ensuring performance of the non-channel member (for example, with respect to rigidity).

In view of the above problem, the present disclosure aims to provide a medical device and a manufacturing method thereof that offer a wide choice of materials to improve the performance of the device.

According to a first embodiment, a medical device includes: a first member provided with a body portion and an anchor that includes a resin material different from a resin material of the body portion, the anchor being formed in an integrated manner with the body portion and interlinked to the body portion; and a second member provided with a connecting portion that includes a resin material that is the same as the resin material of the anchor and is connected to the anchor.

In one aspect, the medical device includes a channel internally, one of the first member and the second member is a channel member that faces the channel, and the other of the first member and the second member is a non-channel member that does not face the channel.

In one aspect, the body portion cooperates with the anchor to form a ring-shaped portion extending in a peripheral direction about a central axis, and the anchor is interlinked to the body portion in the ring-shaped portion, being configured to prevent the body portion from moving in a direction apart from the connecting portion of the second member along the central axis.

In one aspect, the body portion cooperates with the anchor to form a ring-shaped portion extending in a peripheral direction about a central axis, and the anchor is interlinked to the body portion in the ring-shaped portion, being configured to prevent the body portion from rotating toward both sides in the peripheral direction about the central axis.

In one aspect, the medical device includes a valve body sandwiched and held by the first member and the second member.

According to a second embodiment, a medical device includes an internal channel; a first material portion that faces the channel and that includes a continuous resin material; and a second material portion that does not faces the channel and that includes a continuous resin material different from the resin material of the first material portion, wherein one of the first material portion and the second material portion includes an anchor that is formed in an integrated manner and interlinked to the other of the first material portion and the second material portion.

In one aspect, the other of the first material portion and the second material portion cooperates with the anchor to form a ring-shaped portion extending in a peripheral direction about a central axis, and the anchor is interlinked to the other of the first material portion and the second material portion in the ring-shaped portion, being configured to prevent the other of the first material portion and the second material portion from moving in a direction apart from one of the first material portion and second material portion along the central axis.

In one aspect, the other of the first material portion and the second material portion cooperates with the anchor to form a ring-shaped portion extending in a peripheral direction about a central axis, and the anchor is interlinked to the other of the first material portion and the second material portion in the ring-shaped portion, being configured to prevent the other of the first material portion and the second material portion from rotating toward both sides in the peripheral direction about the central axis.

In one aspect, the medical device includes a valve body sandwiched and held by the first material portion and the second material portion.

In another embodiment, a method is provided for manufacturing a medical device that includes: a first member provided with a body portion and an anchor that includes a resin material different from a resin material of the body portion and is interlinked to the body portion; and a second member provided with a connecting portion that includes a resin material that is the same as the resin material of the anchor. The manufacturing method includes: a primary injection step in which one of the anchor and the body portion is formed by injection molding; secondary injection step in which the other of the anchor and the body portion is formed by injection molding while said one of the anchor and the body portion is disposed in a die; and a connection step in which the anchor of the first member obtained in the primary injection step or the secondary injection step is connected to the connecting portion of the second member.

According to certain embodiments of the present disclosure, there is provided a medical device and a manufacturing method thereof that offer a wide choice of materials to improve the performance of the device.

DETAILED DESCRIPTION

Figure 1:
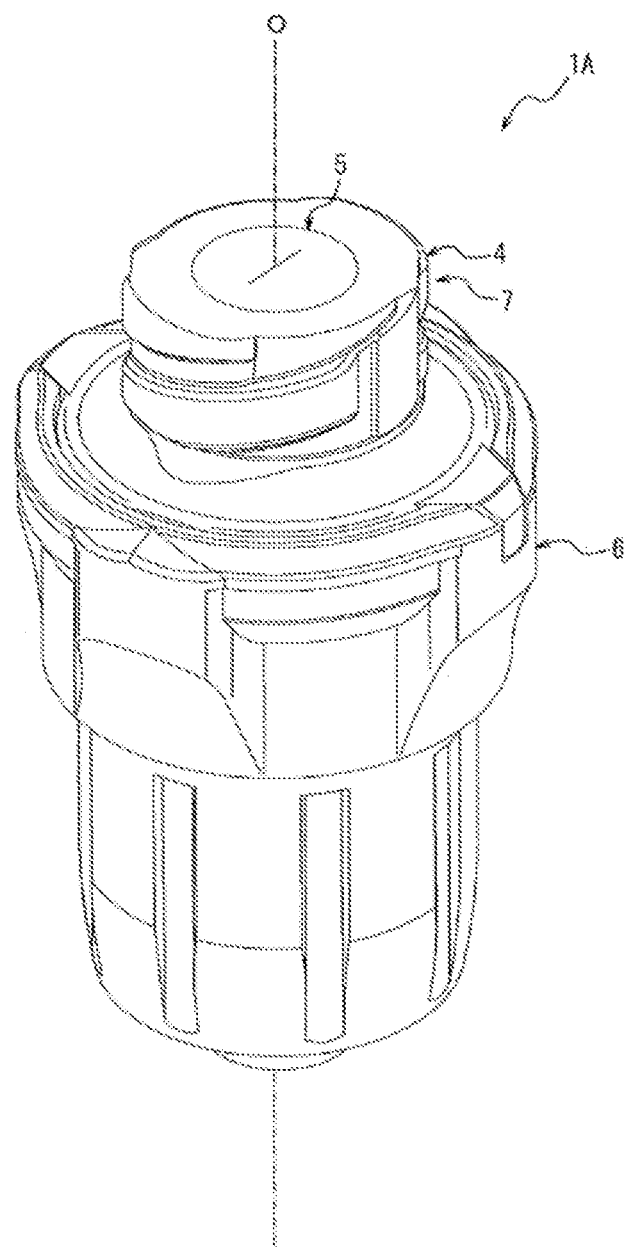
FIG. 1 is a perspective view of a medical device according to a first embodiment.

Hereinafter, a medical device and a manufacturing method thereof according to various embodiments will be described in detail with reference to the drawings. In this specification, a "vertical direction" refers to a direction along a central axis of a ring-shaped portion of a first member, "upward" refers to a direction from a channel toward a valve body, and "downward" refers to the direction opposite the upward direction. In other words, "upward" is the upper side in FIG. 4, while "downward" is the lower side in FIG. 4. In this specification, the "longitudinal section" refers to a cross section including the central axis.

First, referring to FIGS. 1 to 7B, a medical device 1A according to a first embodiment will be described in detail. As shown in FIGS. 1 to 4, the medical device 1A according to this embodiment includes a cap member 4 corresponding to a first member provided with a body portion 9 and an anchor 10. The anchor 10 includes a resin material different from that of the body portion 9, being formed in an integrated manner with the body portion 9 and interlinked to the body portion 9. The medical device 1A includes a valve support member 3 corresponding to a second member provided with a ring-shaped groove 22. The ring-shaped groove 22 includes a resin material that is the same as that of the anchor 10 and functions as a connecting portion connected to the anchor 10. The medical device 1A also includes a valve body 5 and a holder 6. The valve body 5 is sandwiched and held by the valve support member 3 and the cap member 4. In this embodiment, the cap member 4 corresponding to the first member is a non-channel member that does not face a channel 2 formed inside the medical device 1A. In this embodiment, the valve support member 3 corresponding to the second member is a channel member that faces the channel 2. The medical device 1A includes a closed type female connector 7 provided with the valve support member 3, the cap member 4, and the valve body 5. The medical device 1A also includes an open type male connector 8 provided with the holder 6. In this embodiment, the medical device 1A is an I-type connector including two connectors arranged concentrically with each other.

In this embodiment, the cap member 4 is provided with the body portion 9 including the resin material different from that of the valve support member 3; and the anchor 10 including the resin material that is the same as that of the valve support member 3, being interlinked to the body portion 9. With the anchor 10 involved, the cap member 4 and the valve support member 3 are connected to each other by welding (for example, ultrasonic welding). With the anchor 10 involved, the cap member 4 and the valve support member 3 may be connected to each other by means other than welding (for example, using an adhesive).

The valve support member 3 faces the channel 2 so that the valve support member 3 includes a first resin material having chemical resistance. In this embodiment, the first resin material is polypropylene (PP) having excellent chemical resistance. The first resin material is not limited to PP but may be, for example, polyethylene, polytetrafluoroethylene (PTFE), vinyl chloride, nylon, or ABS resin. To improve rigidity, for example, the valve support member 3 may contain a fibrous filler such as glass fiber or carbon fiber. The valve support member 3 may contain various additives to improve material properties at the time of manufacturing or to improve mechanical or chemical properties of the product. The valve support member 3 may be obtained by, for example, injection molding of the first resin material.

The anchor 10 of the cap member 4 includes the first resin material that is the same as that of the valve support member 3, in order to ensure high connection strength to the valve support member 3. To improve rigidity, for example, the anchor 10 may contain a fibrous filler such as glass fiber or carbon fiber. The anchor 10 may contain various additives to improve material properties at the time of manufacturing or to improve mechanical or chemical properties of the product.

The body portion 9 of the cap member 4 includes a second resin material having rigidity higher than the first resin material. In this embodiment, the second resin material is polycarbonate (PC) having excellent rigidity. The second resin material is not limited to PC but may be, for example, cyclic polyolefin or acrylic resin. To improve rigidity, for example, the body portion 9 may contain a fibrous filler such as glass fiber or carbon fiber. The body portion 9 may contain various additives to improve material properties at the time of manufacturing or to improve mechanical or chemical properties of the product.

The cap member 4 is obtained by two-step injection molding: for example, the anchor 10 is obtained by injection molding of the first resin material, and while the anchor 10 is disposed in a die, the second resin material is injected into the die so that the body portion 9 is formed in an integrated manner with the anchor 10. The cap member 4 may be obtained by insert molding. In that case, the anchor 10 obtained by injection molding of the first resin material is inserted into a die, and the second resin material is injected into the die. The cap member 4 may be obtained by two-color molding. In that case, the anchor 10 obtained by injection molding of the first resin material is left in a die, and the second resin material is injected into the die.

Figure 2:
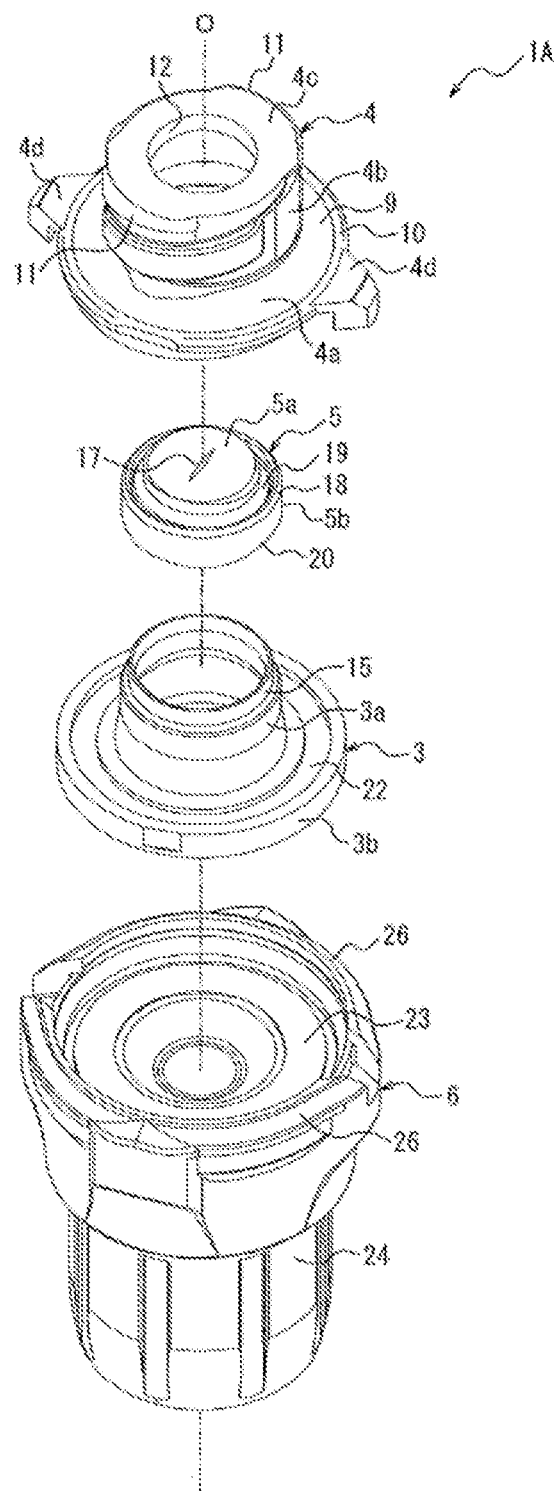
FIG. 2 is an exploded perspective view of the medical device shown in FIG. 1.
Figure 3:
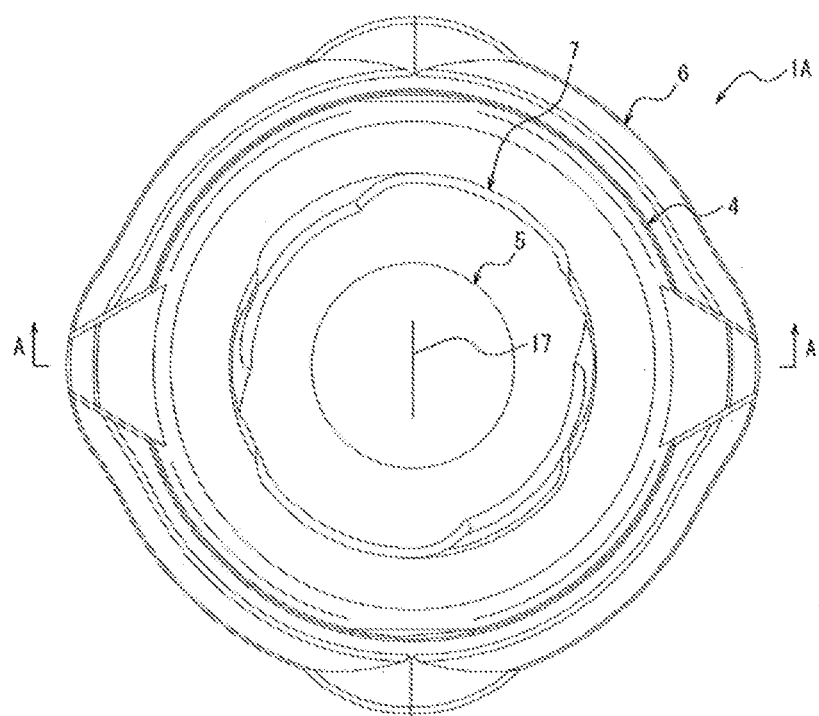
FIG. 3 is a top view of the medical device shown in FIG. 1.
Figure 6:
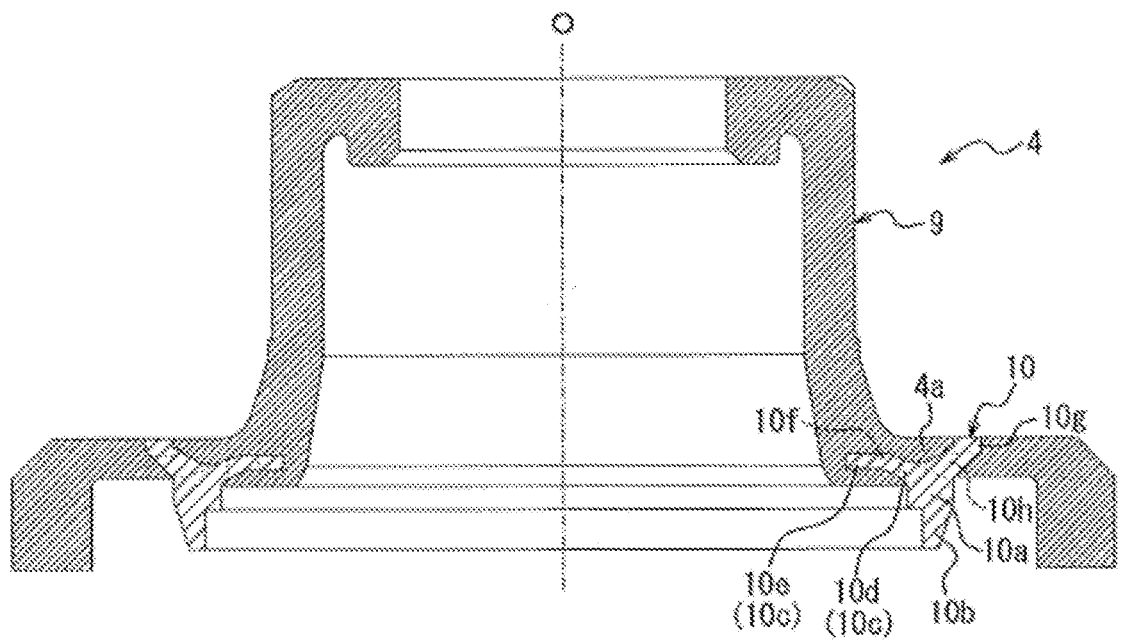
FIG. 6 is a longitudinal sectional view showing that the cap member shown in FIG. 1 is in a state before connection.
Figure 7A:
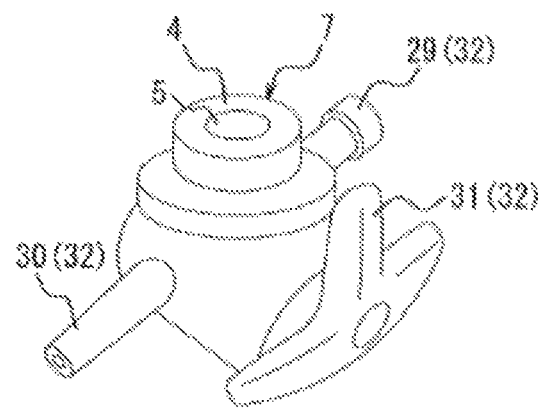
FIGS. 7A and 7B are perspective views schematically showing another example of the medical device shown in FIG. 1.
Figure 7B:
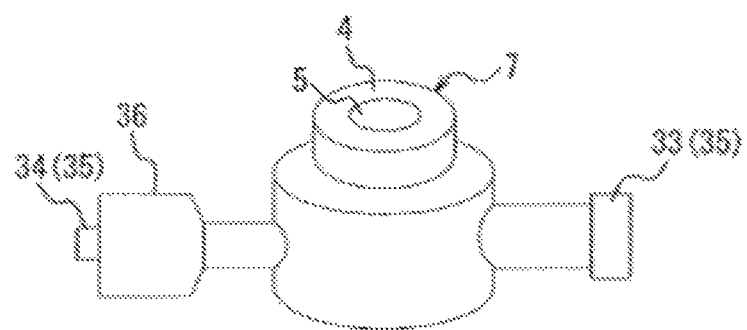
Figure 8:
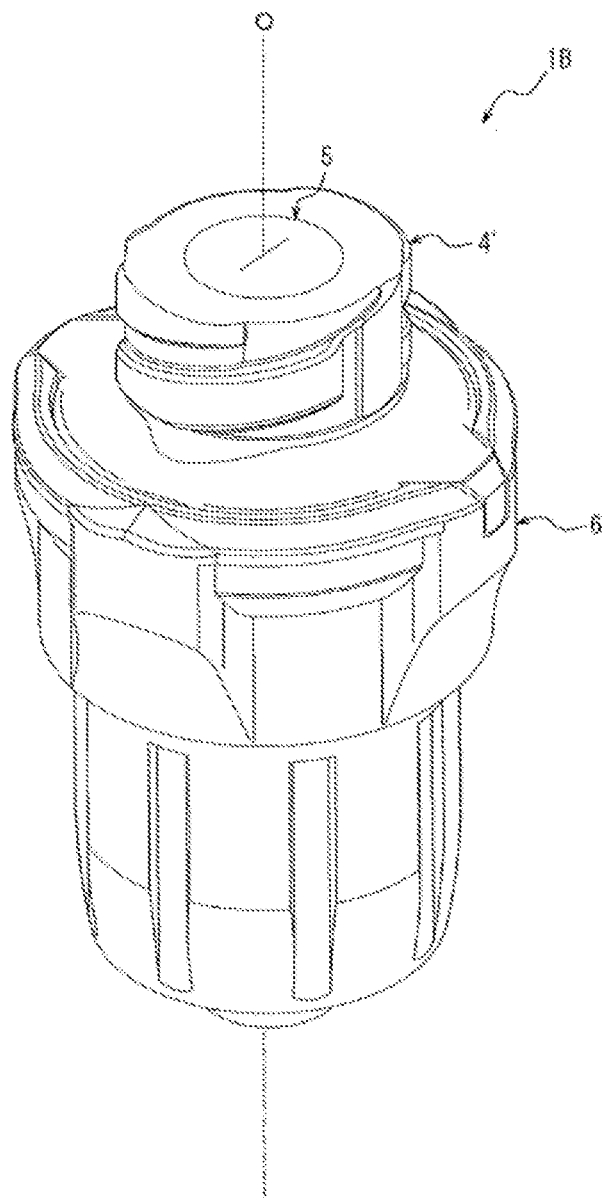
FIG. 8 is a perspective view of a medical device according to a second embodiment.

As shown in FIGS. 2 and 6, the body portion 9 of the cap member 4 cooperates with the anchor 10 to form an upper flange 4a corresponding to a ring-shaped portion that extends in a peripheral direction about a central axis O. The upper flange 4a is shaped into an annular flange. However, the shape of the upper flange 4a may be changed appropriately. In the upper flange 4a, the anchor 10 is interlinked to the body portion 9 so as to prevent the body portion 9 from moving toward both sides in an axial direction along the central axis O (that is, upward and downward) and toward both sides in the peripheral direction about the central axis O (that is, clockwise and counterclockwise). In the upper flange 4a, note that the anchor 10 may be interlinked to the body portion 9 so as to prevent the body portion 9 from moving toward either one of both sides in the axial direction along the central axis O or both sides in the peripheral direction about the central axis O. Furthermore, in the upper flange 4a, the anchor 10 may be interlinked to the body portion 9 so as to prevent the body portion 9 from moving only upward in the axial direction along the central axis O (that is, a direction apart from the ring-shaped groove 22 of the valve support member 3 along the central axis O).

Figure 5:
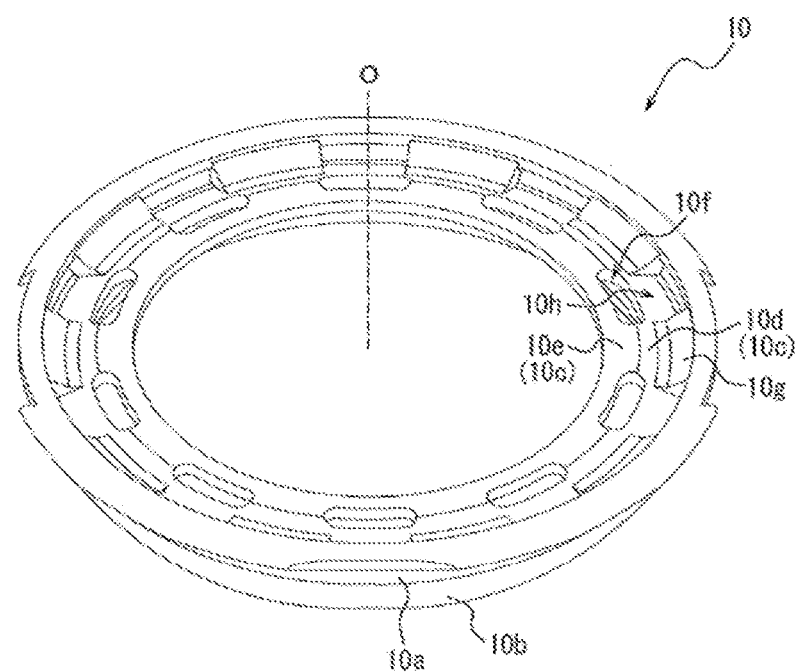
FIG. 5 is a perspective view showing that an anchor in a cap member shown in FIG. 1 is in a state before connection.

In this specification, the expression "interlinked to the body portion 9 so as to prevent the body portion 9 from moving toward both sides in the axial direction along the central axis O" indicates that the anchor 10 includes a portion that is sandwiched by the body portion 9 from both sides in the axial direction and/or a portion that sandwiches the body portion 9 from both sides in the axial direction. As shown in FIGS. 5 to 6, in this embodiment, the anchor 10 includes a through hole 10h oriented in a direction inclined relative to the central axis O, and the anchor 10 is interlinked to the body portion 9 through the through hole 10h. The through hole 10h may be oriented in a direction perpendicular to the central axis O. In this manner, the anchor 10 and the body portion 9 are interlinked to each other through the through hole oriented in the direction inclined relative to the central axis O or in the direction perpendicular to the central axis O. Therefore, the anchor 10 is effectively prevented from falling off the body portion 9 toward both sides in the axial direction along the central axis O.

In this specification, the expression "interlinked to the body portion 9 so as to restrict the body portion 9 from moving toward both sides in the peripheral direction about the central axis O" indicates that the anchor 10 includes a portion that is sandwiched by the body portion 9 from both sides in the peripheral direction and/or a portion that sandwiches the body portion 9 from both sides in the peripheral direction. As shown in FIGS. 5 to 6, in this embodiment, the anchor 10 includes the through hole 10h and a through hole 10f oriented in a direction perpendicular to the peripheral direction about the central axis O, and the anchor 10 is interlinked to the body portion 9 through the through hole 10f and the through hole 10h. The through hole 10f and the through hole 10h may be oriented in a direction inclined relative to the peripheral direction about the central axis O. In this manner, the anchor 10 and the body portion 9 are interlinked to each other through the through hole oriented in the direction perpendicular to the peripheral direction about the central axis O or in the direction inclined relative to the peripheral direction about the central axis O. Therefore, the anchor 10 is effectively prevented from falling off the body portion 9 toward both sides in the peripheral direction about the central axis O.

As shown in FIGS. 5 and 6, the anchor 10 includes a base portion 10a that has an annular shape extending in the peripheral direction about the central axis O and has an all-around rectangular longitudinal section. A lower end of the base portion 10a is interlinked to a leading end portion 10b. The leading end portion 10b has a cylindrical shape extending in the peripheral direction about the central axis O and has a thickness that reduces downward. An inner periphery of the leading end 10b portion is linked to a lower edge of an inner periphery of the base portion 10a, with a stepped involved, so that the inner periphery of the leading end portion 10b expands in diameter. Furthermore, the leading end portion 10b has a constant inner diameter in the vertical direction. An outer periphery of the leading end portion 10b has a conical shape that tapers downward from a lower end of an outer periphery of the base portion 10a. The base portion 10a and the leading end 10b are exposed from the body portion 9.

An annular inward flange portion 10c is interlinked to an upper end of the base portion 10a. The annular inward flange portion 10c extends radially inward about the central axis O from the upper end of the base portion 10a and extends in the peripheral direction about the central axis O. The inward flange portion 10c includes an inner inclined portion 10d and an inner horizontal portion 10e. The inner inclined portion 10d is inclined upward from the upper end of the base portion 10a, being oriented radially inward about the central axis O. The inner horizontal portion 10e extends horizontally from an inner peripheral edge of the inner inclined portion 10d, being oriented radially inward. The inward flange portion 10c includes a plurality of (more specifically, ten) through holes 10f disposed in an interlinked portion between the inner inclined portion 10d and the inner horizontal portion 10e at regular intervals in the peripheral direction about the central axis O. The inward flange 10c is sandwiched by the body portion 9 from both sides in the vertical direction. The inside of the plurality of through holes 10f is closed by a part of the body portion 9. The inward flange 10c portion is entirely buried in the body portion 9.

An annular outward flange portion 10g is interlinked to an outer peripheral edge of the inward flange portion 10c. The annular outward flange 10g extends radially outward about the central axis O from the outer peripheral edge and extends in the peripheral direction about the central axis O. The outward flange portion 10g is inclined upward from the outer peripheral edge of the inward flange portion 10c, being oriented radially outward about the central axis O. The outward flange portion 10g includes a plurality of (more specifically, ten) through holes 10h disposed at regular intervals in the peripheral direction about the central axis O. The plurality of through holes 10h formed in the outward flange portion 10g is aligned in the radial direction with the plurality of through holes 10f formed in the inward flange portion 10c. The inside of the plurality of through holes 10h is closed by a part of the body portion 9. An upper end surface and a part of an outer periphery of the outward flange 10g are exposed from the body portion 9, and the other parts are buried in the body portion 9 (see FIGS. 2 and 5).

The shape of the anchor 10 may be changed appropriately. For example, the base portion 10a may have a ring shape other than the annular shape. The longitudinal section of the base portion 10a is not limited to the rectangular shape. The shape of the leading end portion 10b may be changed appropriately. The inward flange portion 10c may have a ring shape other than the annular shape. The inward flange portion 10c, as a whole, may extend horizontally or may be inclined relative to the horizontal surface. The number of through holes 10f formed in the inward flange portion 10c may be increased or decreased. The plurality of through holes 10f may not be disposed at regular intervals in the peripheral direction. The inward flange portion 10c may not include the through holes 10f. The outward flange portion 10g may have a ring shape other than the annular shape. The outward flange 10g may extend horizontally. The number of through holes 10h formed in the outward flange portion 10g may be increased or decreased. The plurality of through holes 10h may not be disposed at regular intervals in the peripheral direction. The outward flange portion 10g may not include the through holes 10h. The anchor 10 may be provided with one of the inward flange portion 10c or the outward flange portion 10g. Instead of the inward flange portion 10c and the outward flange portion 10g, for example, the anchor 10 may be provided with a ring-shaped upright wall interlinked to the body portion 9. The upright wall extends upward in parallel with the central axis O from the upper end of the base portion 10a and extends in the peripheral direction about the central axis O. In this case, the upright wall may include a plurality of through holes disposed at intervals in the peripheral direction about the central axis O.

Figure 4:
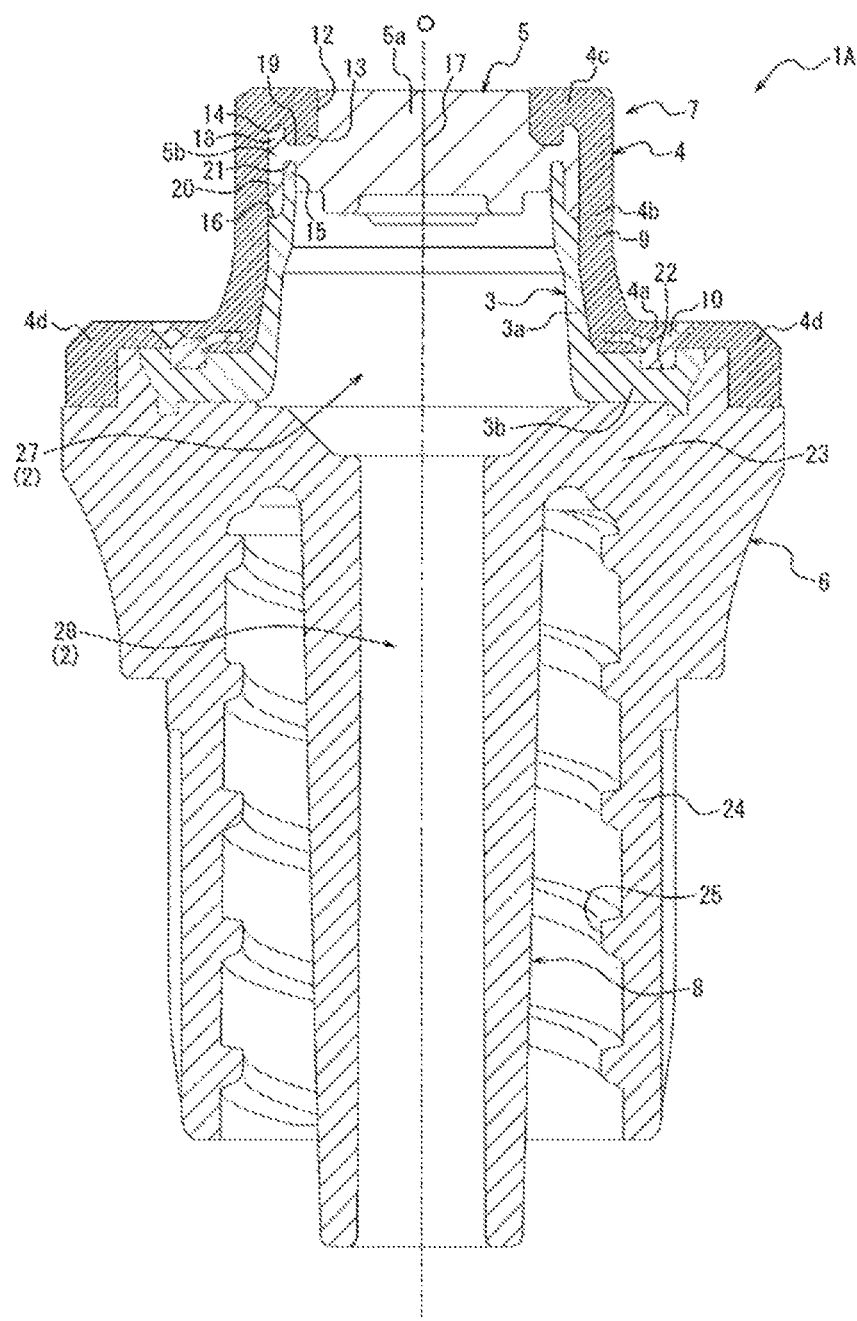
FIG. 4 is a cross-sectional view taken along line A-A of FIG. 3.

As shown in FIGS. 2 and 4, the body portion 9 of the cap member 4 includes a cylindrical outer peripheral wall 4b and an annular top wall 4c. The outer peripheral wall 4b extends upward from an inner peripheral edge of the upper flange 4a and extends in the peripheral direction about the central axis O, and the top wall 4c extends radially inward from the upper edge of the outer peripheral wall 4b and extends in the peripheral direction about the central axis O. On the outer peripheral edge of the upper flange 4a, the body portion 9 of the cap member 4 has a pair of projecting members 4d extending radially outward from two positions opposed to each other across the central axis O. The number of projecting members 4d may be changed appropriately. The projecting members 4d may not be provided in the cap member 4. An outer periphery of the outer peripheral wall 4b is provided with a male thread 11 that enables luer locking. In this embodiment, the male thread 11 has double threads. However, the shape of the male thread 11 may be changed appropriately. Instead of the male thread 11, the cap member 4 may be provided with an engagement portion, other than a screw, which enables engagement to hold a male luer. The cap member 4 may not be provided with an engagement portion.

The body portion 9 of the cap member 4 includes a connecting port 12 that fits with the male luer. The connecting port 12 is formed by an inner periphery of the annular top wall 4c. In this embodiment, the connecting port 12 has a constant inner diameter (for example, 4.15 mm) in the vertical direction. However, the shape of the connecting port 12 may be changed appropriately. For example, the connecting port 12 may have a tapered shape that decreases downward in diameter. A bottom surface of the top wall 4c is provided with an upper ring-shaped protrusion 13 having a cylindrical shape centering on the central axis O. An outer periphery of the upper ring-shaped protrusion 13, a part of the bottom surface of the top wall 4c that is placed radially outward with respect to the upper ring-shaped protrusion 13, and a part of an inner periphery of the outer peripheral wall 4b that is opposed to the outer periphery of the upper ring-shaped protrusion 13 forms an upper support recess 14 having an annular shape.

As shown in FIGS. 2 and 4, the valve support member 3 includes an inner peripheral wall 3a and an annular lower flange 3b. The inner peripheral wall 3a overlaps with the inner periphery of the outer peripheral wall 4b of the cap member 4, and the lower flange 3b extends radially outward from a lower end of the inner peripheral wall 3a and contacts with a bottom surface of the upper flange 4a of the cap member 4. A top surface of the inner peripheral wall 3a is provided with a lower ring-shaped protrusion 15 having a cylindrical shape centering on the central axis O. An outer periphery of the lower ring-shaped protrusion 15, a part of the top surface of the inner peripheral wall 3a that is placed radially outward with respect to the lower ring-shaped protrusion 15, and a part of the inner periphery of the outer peripheral wall 4b of the cap member 4 that is opposed to the outer periphery of the lower ring-shaped protrusion 15 form a lower support recess 16 having an annular shape.

As shown in FIGS. 2 and 4, the valve body 5 is disposed in the connecting port 12. The valve body 5 includes a columnar valve body portion 5a configured to close the connecting port 12; and an annular valve support 5b extending radially outward from an outer periphery of the valve body portion 5a. The valve body portion 5a includes a slit 17 that is pushed open by the male luer inserted into the connecting port 12. In this embodiment, the slit 17 is formed in a straight line in a top view. However, the shape of the slit 17 may be changed appropriately. For example, the slit 17 may have a Y shape in the top view.

A top surface of the valve support 5b is provided with an upper support protrusion 18 having a cylindrical shape centering on the central axis O. An inner periphery of the upper support protrusion 18, and a part of the top surface of the valve support 5b that is placed radially inward with respect to the upper support protrusion 18, and a part of the outer periphery of the valve body portion 5a that is opposed to the inner periphery of the upper support protrusion 18 form an upper ring-shaped recess 19 having an annular shape. The upper support protrusion 18 is disposed in the upper support recess 14. The upper ring-shaped protrusion 13 is disposed in the upper ring-shaped recess 19. A bottom surface of the valve support 5b is provided with a lower support protrusion 20 having a cylindrical shape centering on the central axis O. An inner periphery of the lower support protrusion 20, and a part of the bottom surface of the valve support 5b that is placed radially inward with respect to the lower support protrusion 20, and a part of the outer periphery of the valve body portion 5a that is opposed to the inner periphery of the lower support protrusion 20 form a lower ring-shaped recess 21 having an annular shape. The lower support protrusion 20 is disposed in the lower support recess 16. The lower ring-shaped protrusion 15 is disposed in the lower ring-shaped recess 21. The valve body 5 is obtained by injection molding using a material such as rubber or a thermoplastic elastomer.

As shown in FIGS. 2 and 4, a top surface of the lower flange 3b of the valve support member 3 includes the ring-shaped groove 22. The ring-shaped groove 22 has an annular shape extending in the peripheral direction about the central axis O and has an all-around rectangular longitudinal section. The ring-shaped groove 22 includes the base portion 10a and the leading end portion 10b (see FIG. 6) of the anchor 10 disposed therein. The leading end portion 10b of the anchor 10 is fused by, for example, ultrasonic waves and deformed to fill the inside of the ring-shaped groove 22, and then, cooled and solidified. In this manner, the valve support member 3 and the cap member 4 are connected to each other through the anchor 10 while sandwiching the valve body 5. When the leading end potion 10b of the anchor 10 is fused and deformed to fill the inside of the ring-shaped groove 22, a distance between the upper ring-shaped protrusion 13 and the lower ring-shaped protrusion 15 is reduced. Therefore, a part disposed between the upper ring-shaped recess 19 and the lower ring-shaped recess 21 of the valve body 5 is compressed by the upper ring-shaped protrusion 13 and the lower ring-shaped protrusion 15. Accordingly, the valve body 5 is firmly fixed to the valve support member 3 and the cap member 4. Note that the part disposed between the upper ring-shaped recess 19 and the lower ring-shaped recess 21 of the valve body 5 may not be compressed. The anchor 10 and the valve support member 3 may be connected to each other by means other than welding (for example, using an adhesive).

As shown in FIGS. 2 and 4, the holder 6 is a single-piece member that faces the channel 2. The holder 6 includes the first resin material that is the same as that of the valve support member 3, in order to ensure high connection strength to the valve support member 3. To improve rigidity, for example, the holder 6 may contain a fibrous filler such as glass fiber or carbon fiber. The holder 6 may contain various additives to improve material properties at the time of manufacturing or to improve mechanical or chemical properties of the product. The holder 6 may be obtained by, for example, injection molding of the first resin material.

The holder 6 is provided with an annular interlinked wall 23, a male connector 8, and a locking cylinder 24 for luer locking. The male connector 8 includes a male luer hanging down from an inner peripheral edge of the interlinked wall 23, and the locking cylinder 24 for luer locking is hanging down from an outer peripheral edge of the interlinked wall 23. An inner periphery of the locking cylinder 24 is provided with an internal thread 25 that enables luer locking. An outer peripheral edge in a top surface of the interlinked wall 23 is provided with a pair of upright walls 26 that has an arc shape centering on the central axis O in a top view. The upper flange 4a of the cap member 4 and the lower flange 3b of the valve support member 3 are disposed radially inward with respect to the pair of upright walls 26. Between the pair of upright walls 26, the pair of projecting members 4d is arranged. A bottom surface of the lower flange 3b of the valve support member 3 and the top surface of the interlinked wall 23 are connected to each other by welding. An outer periphery of the lower flange 3b of the valve support member 3 and an inner periphery of the pair of upright walls 26 are connected to each other by welding. The lower flange 3b of the valve support member 3 and the holder 6 may be connected to each other by means other than welding (for example, using an adhesive).

The medical device 1A includes a female connector channel 27 that is defined by a bottom surface of the valve body portion 5a of the valve body 5, an inner periphery of the inner peripheral wall 3a of the valve support member 3, and the top surface of the interlinked wall 23 of the holder 6. The female connector channel 27 communicates with a male connector channel 28 defined by an inner periphery of the male connector 8. The channel 2 inside the medical device 1A includes the female connector channel 27 and the male connector channel 28. When the male luer is inserted into the connecting port 12, the valve body portion 5a of the valve body 5 pushed by the male luer is pushed downward and deformed, which causes the male luer to fit into the connecting port 12. Deformation of the valve body portion 5a opens the slit 17 of the valve body portion 5a so that the channel inside the male luer communicates with the female connector channel 27. In a case where the male luer includes a locking cylinder for luer locking, the connection between the male luer and the female connector 7 is held more reliably when the locking cylinder is screwed in the male thread 11. Particularly, in this embodiment, the body portion 9 of the cap member 4 includes the second resin material having relatively high rigidity, which imparts the male thread 11 for luer locking with relatively high rigidity and prevents the male thread 11 from being damaged. In the medical device 1A, the male luer may be held in a state connected to the connecting port 12 without being fitted into the connecting port 12 but, for example, with the locking cylinder being screwed in the male thread 11.

As shown in FIG. 4, the medical device 1A is provided with a first material portion facing the channel 2 and including a continuous first resin material. In this embodiment, the first material portion includes the anchor 10, the valve support member 3, and the holder 6. The medical device 1A is provided with a second material portion that does not face the channel 2 and that includes a continuous second resin material different from the first material portion. In this embodiment, the second material portion includes the body portion 9 of the cap member 4. In this embodiment, the first material portion includes the anchor 10 formed in an integrated manner and interlinked to the second material portion. The second material portion and the anchor 10 cooperates to form the upper flange 4a corresponding to the ring-shaped portion extending in the peripheral direction about the central axis O. In the upper flange 4a, the anchor 10 is interlinked to the second material portion so as to prevent the second material portion from moving toward both sides in the axial direction along the central axis O and toward both sides in the peripheral direction about the central axis O. In the upper flange 4a, note that the anchor 10 may be interlinked to the second material portion so as to prevent the second material portion from moving toward either one of both sides in the axial direction along the central axis O or both sides in the peripheral direction about the central axis O. Furthermore, in the upper flange 4a, the anchor 10 may be interlinked to the second material portion so as to prevent the second material portion from moving only upward in the axial direction along the central axis O (that is, a direction apart from the first material portion along the central axis O). The valve body 5 is sandwiched and held by the first material portion and the second material portion.

In the medical device 1A according to this embodiment, the cap member 4 corresponding to the non-channel member is provided with the anchor 10 that includes the resin material different from that of the body portion 9 and is formed in an integrated manner with the body portion 9 and interlinked to the body portion 9, and the valve support member 3 corresponding to the channel member is provided with the connecting portion (ring-shaped groove 22) that includes the resin material that is the same as that of the anchor 10 and is connected to the anchor 10. This makes it possible to improve the rigidity of the cap member 4 while ensuring high connection strength between the cap member 4 and the valve support member 3. In other words, in the medical device 1A according to this embodiment, the first material portion includes the anchor 10 that is formed in an integrated manner and interlinked to the second material portion, so that it is possible to improve the rigidity of the second material portion while preventing the second material portion from falling off first material portion. Therefore, the medical device 1A according to this embodiment offers a wide choice of materials to improve the performance of the device.

As described above, in this embodiment, the medical device 1A is an I-type connector. However, the medical device 1A may be a medical connector of different types such as a three-way stopcock shown in FIG. 7A and a T-shape connector shown in FIG. 7B. The three-way stopcock shown in FIG. 7A includes the closed type female connector 7 including the cap member 4, the valve body 5, and the valve support member 3. In place of the holder 6, the three-way stopcock includes a housing 32 provided with an open type female connector 29, an open type male connector 30, and a lever member 31 for selecting channels. The T-shape connector shown in FIG. 7B includes the closed type female connector 7 including the cap member 4, the valve body 5, and the valve support member 3. In place of the holder 6, the T-shape connector includes a housing 35 provided with an open type female connector 33 and an open type male connector 34. The male connector 34 is provided with a locking cylinder 36 for luer locking.

The shapes of the cap member 4, the valve body 5, and the valve support member 3 may be changed appropriately. The valve support member 3 may be formed in an integrated manner with the holder 6 by, for example, injection molding.

Next, a medical device 1B according to a second embodiment of the present invention will be described in detail with reference to FIGS. 8 to 13. As shown in FIGS. 8 to 11, the medical device 1B according to this embodiment includes a valve support member 3' corresponding to a channel member. The valve support member 3' is a first member provided with a body portion 37 and an anchor 38. The anchor 38 includes a resin material different from that of the body portion 37, being formed in an integrated manner with the body portion 37 and interlinked to the body portion 37. The medical device 1B according to this embodiment also includes a cap member 4' corresponding to a non-channel member. The cap member 4' is a second member provided with a connecting cylinder 39. The connecting cylinder 39 includes a resin material that is the same as that of the anchor 38 and functions as a connecting portion connected to the anchor 38. In other respects, the medical device 1B according to this embodiment has a configuration similar to that of the medical device 1A according to the first embodiment.

Figure 9:
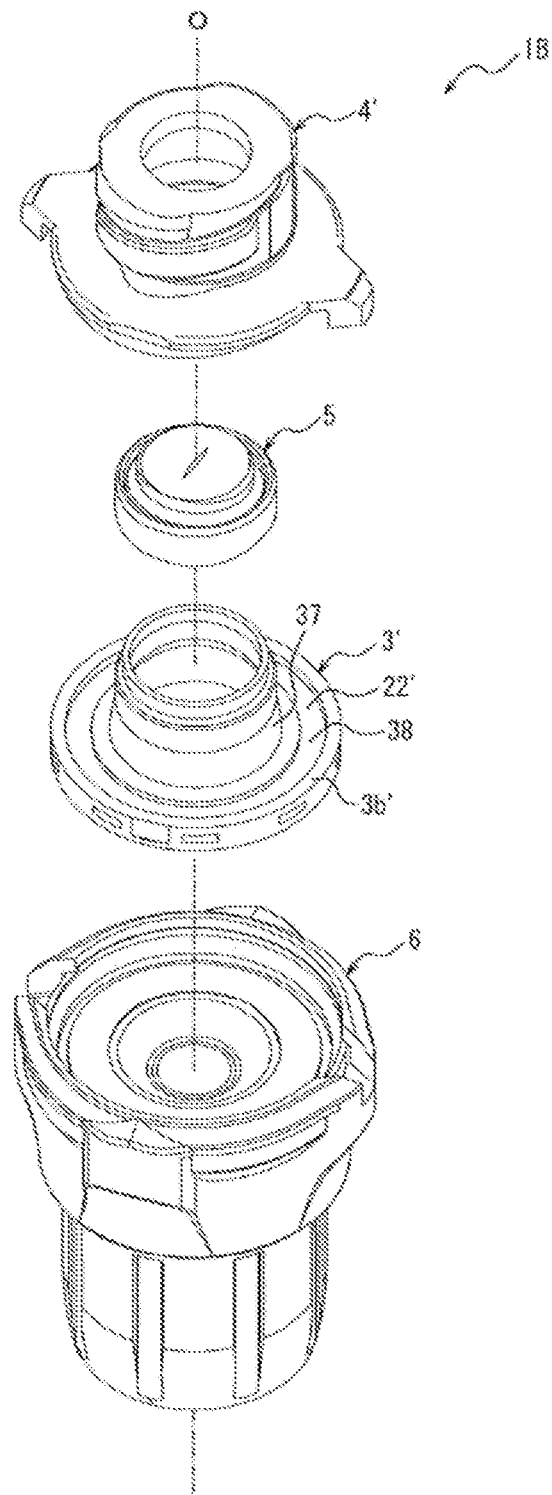
FIG. 9 is an exploded perspective view of the medical device shown in FIG. 8.
Figure 10:
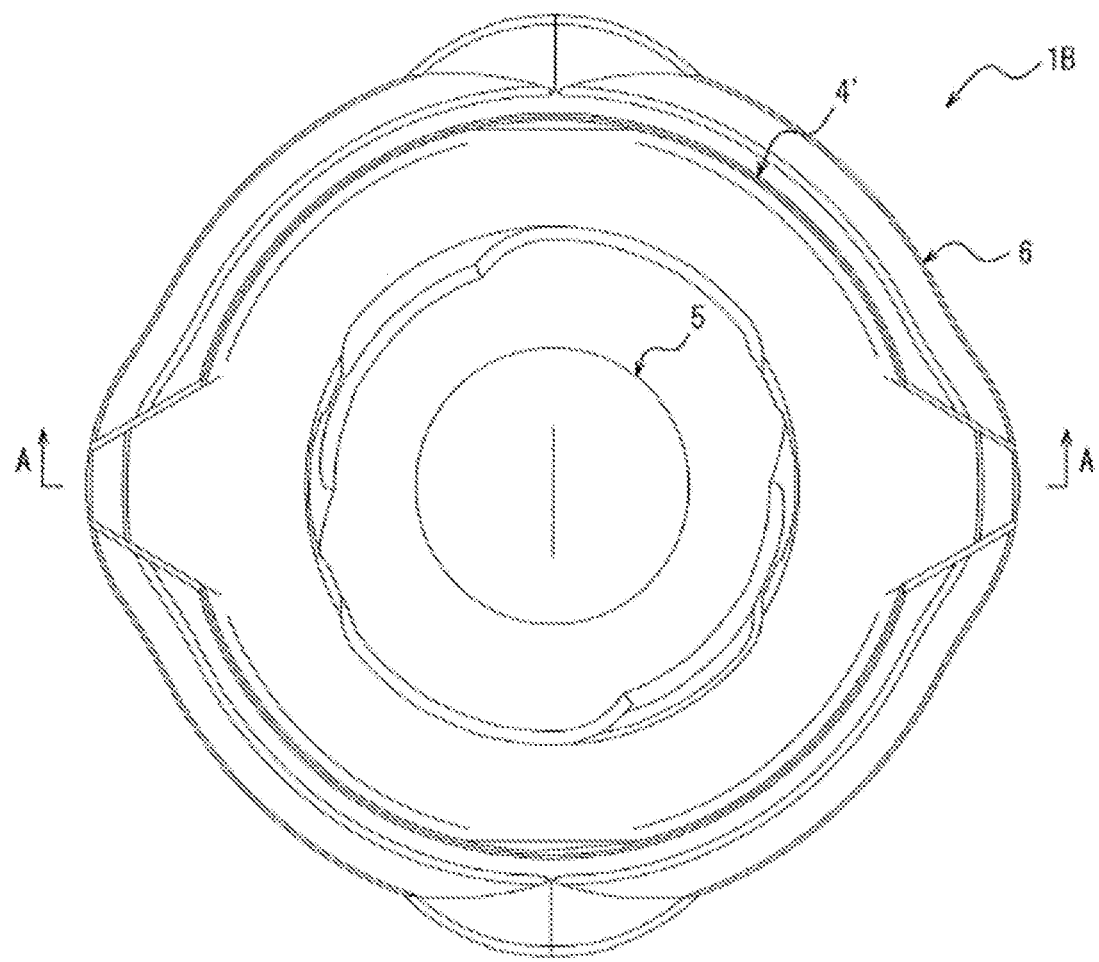
FIG. 10 is a top view of the medical device shown in FIG. 8.
Figure 13:
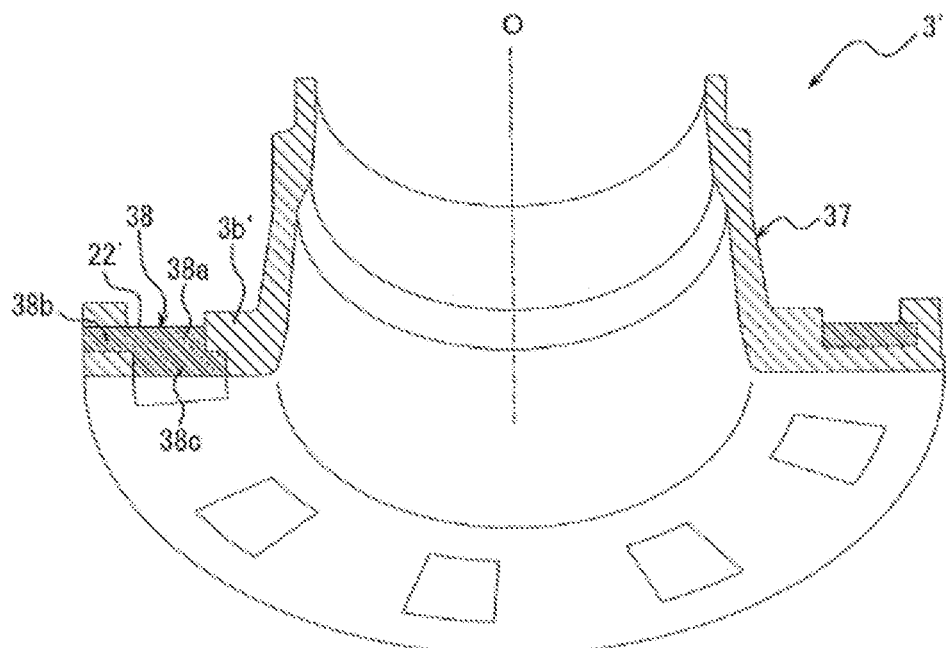
FIG. 13 is a cross-sectional perspective view showing that the valve support member shown in FIG. 8 is in a state before connection.

As shown in FIGS. 9 and 13, in this embodiment, the body portion 37 of the valve support member 3' cooperates with the anchor 38 to forms a lower flange 3b' corresponding to a ring-shaped portion extending in a peripheral direction about a central axis O. In the lower flange 3b', the anchor 38 is interlinked to the body portion 37 so as to prevent the body portion 37 from moving toward both sides in the axial direction along the central axis O and toward both sides in the peripheral direction about the central axis O. In the lower flange 3b', note that the anchor 38 may be interlinked to the body portion 37 so as to prevent the body portion 37 from moving toward either one of both sides in the axial direction along the central axis O or both sides in the peripheral direction about the central axis O. Furthermore, in the lower flange 3b', the anchor 38 may be interlinked to the body portion 37 so as to prevent the body portion 37 from moving only downward in the axial direction along the central axis O (that is, a direction apart from the connecting cylinder 39 of the cap member 4' along the central axis O).

Figure 12:
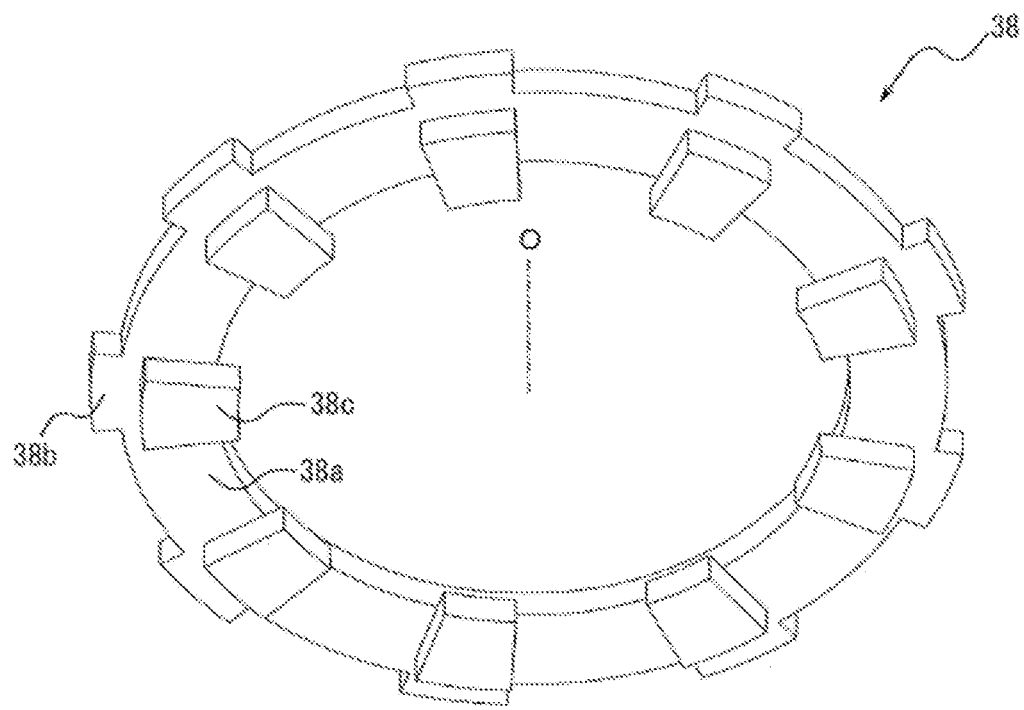
FIG. 12 is a perspective view showing that an anchor in a valve support member shown in FIG. 8 is in a state before connection.

As shown in FIGS. 12 to 13, the anchor 38 includes a base portion 38a that has an annular shape extending in the peripheral direction about the central axis O and has an all-around rectangular longitudinal section. An upper surface of the base 38a is exposed from the lower flange 3b'. The lower flange 3b' includes a ring-shaped groove 22' that includes the upper surface of the base portion 38a as a base portion. The other portion of the base portion 38a is buried in the body portion 37.

A plurality of (more specifically, nine) outer projecting members 38b is interlinked to an outer periphery of the base portion 38a. The outer projecting members 38b are disposed at regular intervals in the peripheral direction about the central axis O, having a plate shape projecting radially outward about the central axis O. Each of the outer projecting members 38b has a thickness equal to that of the base portion 38a. Each of the outer projecting members 38b is sandwiched by the body portion 37 from both sides in the vertical direction. Before the cap member 4' and the valve support member 3' are welded, an outer periphery of each of the outer projecting members 38b is exposed from the body portion 37. The other parts of each of the outer projecting members 38b are buried in the body portion 37.

A plurality of (more specifically, nine) lower projecting members portion 38c is interlinked to a bottom surface of the base 38a. The lower projecting members 38c are disposed at regular intervals in the peripheral direction about the central axis O, having a plate shape projecting radially inward about the central axis O from an inner periphery of the base portion 38a. A bottom surface of each of the lower projecting members 38c is exposed from the body portion 37. The other parts of each of the lower projecting members 38c are buried in the body portion 37. The plurality of lower projecting members 38c is aligned in the radial direction with the plurality of outer projecting members 38b. The plurality of lower projecting members 38c has a width in the peripheral direction equal to that of the plurality of outer projecting members 38b. Each of the lower projecting members 38c has a thickness equal to that of the base 38a.

The anchor 38 includes a second resin material (PC in this embodiment) same as that of the cap member 4'. The body portion 37 includes a first resin material (PP in this embodiment).

The valve support member 3' is obtained by two-step injection molding: for example, the anchor 38 is obtained by injection molding of the second resin material, and while the anchor 38 is disposed in a die, the first resin material is injected thereto so that the body portion 37 is formed in an integrated manner with the anchor 38. The valve support member 3' may be obtained by insert molding. In that case, the anchor 38 obtained by injection molding of the second resin material is inserted into a die, and the first resin material is injected thereto. The valve support member 3' may be obtained by two-color molding. In that case, the anchor 38 obtained by injection molding of the second resin material is left in a die, and the first resin material is injected thereto.

The shape of the anchor 38 may be changed appropriately. For example, the base portion 38a may have a ring shape other than the annular shape. The longitudinal section of the base portion 38a is not limited to the rectangular shape. The shape of the outer projecting members 38b may be changed appropriately. The number of outer projecting members 38b may be increased or decreased. The plurality of outer projecting members 38b may not be disposed at regular intervals in the peripheral direction. The shape of the lower projecting members 38c may be changed appropriately. The number of lower projecting members 38c may be increased or decreased. The plurality of lower projecting members 38c may not be disposed at regular intervals in the peripheral direction.

Figure 11:
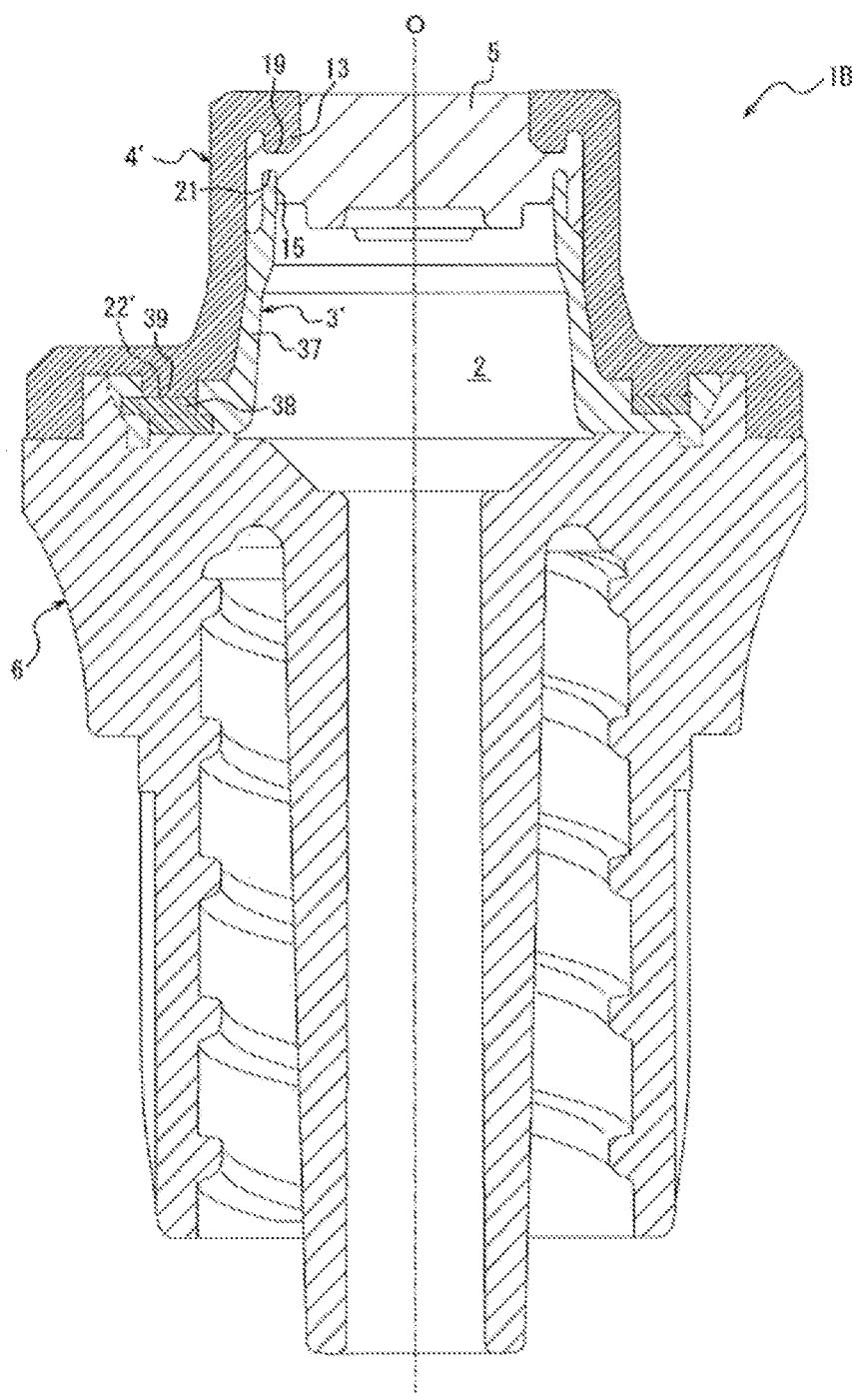
FIG. 11 is a cross-sectional view taken along line A-A of FIG. 10.

As shown in FIG. 11, the cap member 4' includes a cylindrical connecting cylinder 39 projecting downward from a bottom surface of the upper flange 4a' and extending in the peripheral direction about the central axis O. In FIG. 11, the connecting cylinder 39 is fused by, for example, ultrasonic waves and deformed to fill the inside of the ring-shaped groove 22' of the valve support member 3', and then, cooled and solidified. In this manner, the valve support member 3' and the cap member 4' are connected to each other through the anchor 38 while sandwiching the valve body 5. When the connecting cylinder 39 is fused and deformed to fill the inside of the ring-shaped groove 22', a distance between the upper ring-shaped protrusion 13 and the lower ring-shaped protrusion 15 is reduced. Therefore, a part disposed between the upper ring-shaped recess 19 and the lower ring-shaped recess 21 of the valve body 5 is compressed by the upper ring-shaped protrusion 13 and the lower ring-shaped protrusion 15. Accordingly, the valve body 5 is firmly fixed to the valve support member 3' and the cap member 4'. Note that the part disposed between the upper ring-shaped recess 19 and the lower ring-shaped recess 21 of the valve body 5 may not be compressed. The cap member 4' and the anchor 38 may be connected to each other by means other than welding (for example, using an adhesive).

As shown in FIG. 11, the medical device 1B is provided with a first material portion facing a channel 2 and including a continuous first resin material. In this embodiment, the first material portion includes the body portion 37 of the valve support member 3' and the holder 6. The medical device 1B is provided with a second material portion that does not face the channel 2 and that includes a continuous second resin material different from the first material portion. In this embodiment, the second material portion includes the cap member 4' and the anchor 38 of the valve support member 3'. In this embodiment, the second material portion includes the anchor 38 formed in an integrated manner and interlinked to the first material portion. The first material portion and the anchor 38 cooperates to form the lower flange 3b' corresponding to the ring-shaped portion extending in the peripheral direction about the central axis O. In the lower flange 3b', the anchor 38 is interlinked to the first material portion so as to prevent the first material portion from moving toward both sides in the axial direction along the central axis O and toward both sides in the peripheral direction about the central axis O. In the lower flange 3b', note that the anchor 38 may be interlinked to the first material portion so as to prevent the first material portion from moving toward either one of both sides in the axial direction along the central axis O or both sides in the peripheral direction about the central axis O. Furthermore, in the lower flange 3b', the anchor 38 may be interlinked to the first material portion so as to prevent the first material portion from moving only downward in the axial direction along the central axis O (that is, a direction apart from the second material portion along the central axis O). The valve body 5 is sandwiched and held by the first material portion and the second material portion.

In the medical device 1B according to this embodiment, the valve support member 3' corresponding to the channel member is provided with anchor 38 that includes the resin material different from that of the body portion 37 and is formed in an integrated manner with the body portion 37 and interlinked to the body portion 37, and the cap member 4' corresponding to the non-channel member is provided with the connecting portion (connecting cylinder 39) that includes the resin material that is the same as that of the anchor 38 and is connected to the anchor 38. This makes it possible to improve the rigidity of the cap member 4' while ensuring high connection strength between the cap member 4' and the valve support member 3'. In other words, in the medical device 1B according to this embodiment, the second material portion includes the anchor 38 that is formed in an integrated manner and interlinked to the first material portion, so that it is possible to improve the rigidity of the second material portion while preventing the second material portion from falling off first material portion. Therefore, the medical device 1B according to this embodiment offers a wide choice of materials to improve the performance of the device.

In this embodiment, the medical device 1B is as an I-type connector. Similarly to the first embodiment, the medical device 1B may be a medical connector of different types such as the three-way stopcock shown in FIG. 7A and the T-shape connector shown in FIG. 7B.

The shapes of the cap member 4', the valve body 5, and the valve support member 3' may be changed appropriately. The valve support member 3' may be formed in an integrated manner with the holder 6 by, for example, injection molding.

Next, a manufacturing method of a medical device according to the first embodiment of the present invention will be described in detail with reference to FIG. 14. The manufacturing method of a medical device according to this embodiment is a manufacturing method of the medical device 1A shown in FIGS. 1 to 6. However, the medical device 1A according to the first embodiment is not limited to one obtained by the manufacturing method of a medical device according to this embodiment.

Figure 14:
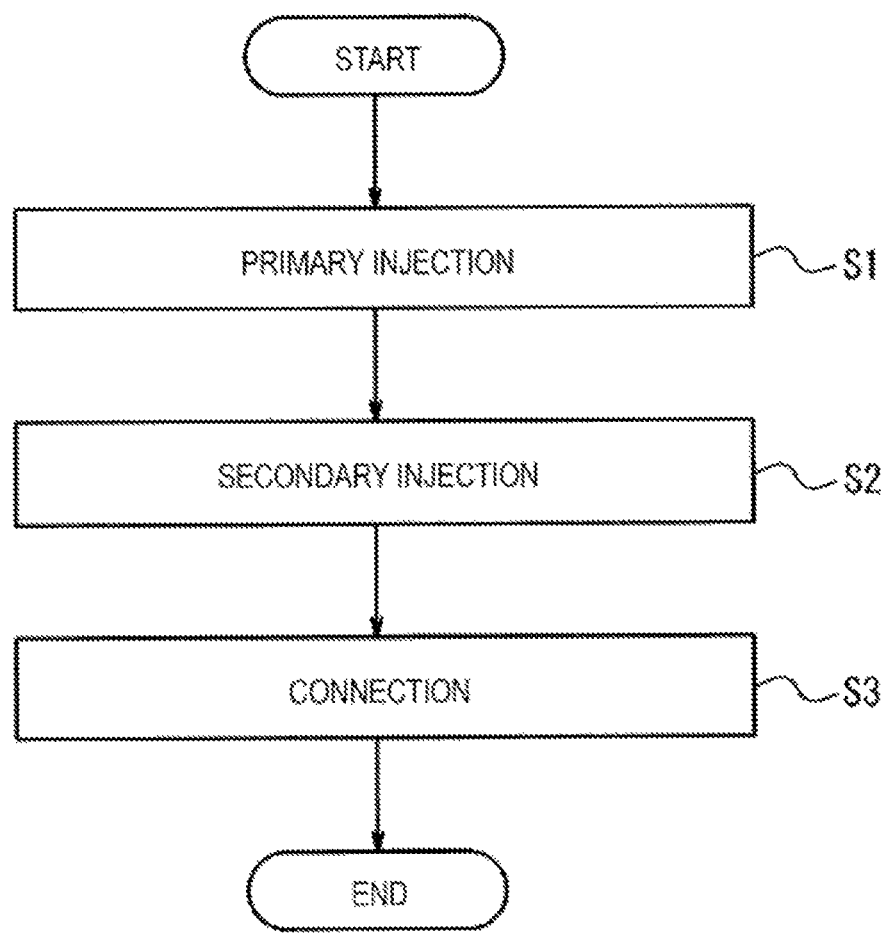
FIG. 14 is a flowchart showing steps in a manufacturing method of a medical device according to the first embodiment and the second embodiment.

As shown in FIG. 14, the manufacturing method of a medical device according to this embodiment involves a primary injection step S1 in which the anchor 10 is formed by injection molding (see FIG. 5); a secondary injection step S2 in which the body portion 9 is formed by injection molding while the anchor 10 is disposed in a die; and a connection step S3 in which the anchor 10 of the cap member 4 (first member) obtained in the secondary injection step S2 is connected to the ring-shaped groove 22 (connecting unit) of the valve support member 3 (second member).

First, in the primary injection step S1, the anchor 10 is formed by injection molding, using the first resin material. To the first resin material, the fibrous filler and/or the additives may be added.

Next, in the secondary injection step S2, the anchor 10 obtained in the primary injection step S1 is inserted into the die, and the body portion 9 is formed in an integrated manner with the anchor 10 by insert molding of the second resin material so as to obtain the cap member 4 (see FIG. 6). To the second resin material, the fibrous filler and/or the additives may be added. In the secondary injection step S2, the cap member 4 may be obtained by forming the body portion 9 in an integrated manner with the anchor 10 by two-color molding where the second resin material is injected to the die while the anchor 10 obtained in the primary injection step S1 is left in the die.

Next, in the connection step S3, the cap member 4 obtained in the secondary injection step S2, the valve support member 3, and the valve body 5 are assembled so that the valve body 5 is sandwiched between the cap member 4 and the valve support member 3. The anchor 10 of the cap member 4 and the ring-shaped groove 22 of the valve support member 3 are welded by, for example, ultrasonic waves so as to obtain an assembly of the cap member 4, the valve support member 3, and the valve body 5. Herein, the anchor 10 and the ring-shaped groove 22 of the valve support member 3 both include the first resin material, which ensures high connection strength therebetween. In the connection step S3, the leading end portion 10b of the anchor 10 is fused by, for example, ultrasonic waves and deformed to fill the inside of the ring-shaped groove 22. Therefore, the distance between the upper ring-shaped protrusion 13 and the lower ring-shaped protrusion 15 may be reduced, and the part disposed between the upper ring-shaped recess 19 and the lower ring-shaped recess 21 of the valve body 5 may be compressed. Accordingly, the valve body 5 is firmly fixed to the valve support member 3 and the cap member 4. In the connection step S3, the anchor 10 and the valve support member 3 may be connected to each other by means other than welding (for example, using an adhesive).

Next, the assembly of the cap member 4, the valve support member 3, and the valve body 5 obtained in the connection step S3 is assembled to the holder 6. The valve support member 3' is welded to the holder 6 by, for example, ultrasonic waves so as to obtain the medical device 1A. Herein, the valve support member 3' and the holder 6 both include the first resin material, which ensures high connection strength therebetween. The valve support member 3 and the holder 6 may be connected to each other by means other than welding (for example, using an adhesive).

Before the connection step S3, the valve support member 3 may be connected to the holder 6, and then, in the connection step S3, the cap member 4 and the valve body 5 may be assembled to the valve support member 3, and the cap member 4 and the valve support member 3 may be connected to each other through the anchor 10.

According to the manufacturing method of a medical device according to this embodiment, there is provided the medical device 1A that offers a wide choice of materials to improve the performance of the device. The manufacturing method of a medical device according to this embodiment may also be used for manufacturing medical devices different from the medical device 1A (for example, a three-way stopcock or a T-shape connector).

Next, a manufacturing method of a medical device according to the second embodiment of the present invention will be described in detail with reference to FIG. 14. The manufacturing method of a medical device according to this embodiment is a manufacturing method of the medical device 1B shown in FIGS. 8 to 13. However, the medical device 1B according to the second embodiment is not limited to one obtained by the manufacturing method of a medical device according to this embodiment.

As shown in FIG. 14, the manufacturing method of a medical device according to this embodiment involves a primary injection step S1 in which the anchor 38 is formed by injection molding (see FIG. 12); a secondary injection step S2 in which the body portion 37 is formed by injection molding while the anchor 38 is disposed in a die; and a connection step S3 in which the valve support member 3' (first member) obtained in the secondary injection step S2 is connected to the connecting cylinder 39 (connecting unit) of the cap member 4' (second member).

First, in the primary injection step S1, the anchor 38 is formed by injection molding, using the second resin material. To the second resin material, the fibrous filler and/or the additives may be added.

Next, in the secondary injection step S2, the anchor 38 obtained in the primary injection step S1 is inserted into the die, and the body portion 37 is formed in an integrated manner with the anchor 38 by insert molding of the first resin material so as to obtain the valve support member 3' (see FIG. 13). To the first resin material, the fibrous filler and/or the additives may be added. In the secondary injection step S2, the valve support member 3' may be obtained by forming the body portion 37 in an integrated manner with the anchor 38 by two-color molding where the first resin material is injected to the die while the anchor 38 obtained in the primary injection step S1 is left in the die.

Next, in the connection step S3, the cap member 4', the valve support member 3' obtained in the secondary injection step S2, and the valve body 5 are assembled so that the valve body 5 is sandwiched between the cap member 4' and the valve support member 3'. The connecting cylinder 39 of the cap member 4' and the anchor 38 of the valve support member 3' are welded by, for example, ultrasonic waves so as to obtain an assembly of the cap member 4', the valve support member 3', and the valve body 5. Herein, the connecting cylinder 39 of the cap member 4' and the anchor 38 both include the second resin material, which ensures high connection strength therebetween. In the connection step S3, the connecting cylinder 39 of the cap member 4'is fused by, for example, ultrasonic waves and deformed to fill the inside of the ring-shaped groove 22'. Therefore, the distance between the upper ring-shaped protrusion 13 and the lower ring-shaped protrusion 15 may be reduced, and the part disposed between the upper ring-shaped recess 19 and the lower ring-shaped recess 21 of the valve body 5 may be compressed. Accordingly, the valve body 5 is firmly fixed to the valve support member 3' and the cap member 4'. In the connection step S3, the cap member 4' and the anchor 38 may be connected to each other by means other than welding (for example, using an adhesive).

Next, the assembly of the cap member 4', the valve support member 3', and the valve body 5 obtained in the connection step S3 is assembled to the holder 6. The body portion 37 of the valve support member 3' and the holder 6 are welded by, for example, ultrasonic waves so as to obtain the medical device 1B. Herein, the body portion 37 of the valve support member 3' and the holder 6 both include the first resin material, which ensures high connection strength therebetween. The body portion 37 of the valve support member 3' and the holder 6 may be connected to each other by means other than welding (for example, using an adhesive).

Before the connection step S3, the body portion 37 of the valve support member 3' may be connected to the holder 6, and then, in the connection step S3, the cap member 4' and the valve body 5 may be assembled to the valve support member 3', and the cap member 4' and the valve support member 3' may be connected to each other through the anchor 38.

According to the manufacturing method of a medical device according to this embodiment, there is provided the medical device 1B that offers a wide choice of materials to improve the performance of the device. The manufacturing method of a medical device according to this embodiment may also be used for manufacturing medical devices different from the medical device 1B (for example, a three-way stopcock or a T-shape connector).

Each of the aforementioned embodiments are merely illustrative of the present invention, and it goes without saying that the present invention may employ various modifications without departing from the gist of the invention.

What is claimed is:

1. A medical device comprising:
   a first member comprising:
      a body portion comprising a cylindrical outer peripheral wall, and
      an anchor comprising an inward flange portion and an outward flange portion,
      wherein a resin material of the anchor is different from a resin material of the body portion,
      wherein the anchor is interlinked to the body portion such that the body portion and the anchor form a flange that extends radially outward from a bottom of the cylindrical outer peripheral wall,
      wherein the outward flange portion of the anchor is exposed from the body portion at an upper surface of the flange, such that the upper surface of the flange is formed of an upward-facing surface of the body portion and an upper-most surface of the anchor, and wherein the inward flange portion of the anchor is sandwiched by the body portion in an axial direction of the first member; and a second member comprising a connecting portion that is connected to a lower portion of the anchor, wherein a resin material of the second member is the same as the resin material of the anchor.

2. The medical device according to claim 1, wherein:
the medical device includes an internal channel,
one of the first member or the second member is a channel member that faces the channel, and
an other of the first member or the second member is a non-channel member that does not face the channel.

3. The medical device according to claim 1, wherein:
the anchor is interlinked to the body portion in the flange, and is configured to prevent the body portion from moving in a direction apart from the connecting portion of the second member along the central axis.

4. The medical device according to claim 1, wherein:
the anchor is interlinked to the body portion in the flange, and is configured to prevent the body portion from rotating toward both sides in the peripheral direction about the central axis.

5. The medical device according to claim 1, wherein the medical device includes a valve body, and wherein a portion of the valve body is sandwiched and held by the first member and the second member.

6. The medical device according to claim 1, wherein an upward-facing surface of the body portion is coplanar with an upper-most surface of the anchor at the upper surface of the flange.

7. The medical device according to claim 1, wherein, at the upper surface of the flange, a first part of the body portion is located radially inward of the anchor, and a second part of the body portion is located radially outward of the anchor.

* * * * *